(12) United States Patent
Brattin

(10) Patent No.: US 10,258,510 B1
(45) Date of Patent: Apr. 16, 2019

(54) SELF-ADHERING OCCLUSION EYE PATCH AND METHOD OF CONSTRUCTING AND USING SAME

(71) Applicant: Paige Brattin, Kamuela, HI (US)

(72) Inventor: Paige Brattin, Kamuela, HI (US)

( * ) Notice: Subject to any disclaimer, the term of this patent is extended or adjusted under 35 U.S.C. 154(b) by 0 days.

(21) Appl. No.: 16/028,266

(22) Filed: Jul. 5, 2018

(51) Int. Cl.
*A61F 9/04* (2006.01)
*A61F 13/02* (2006.01)
*A61F 13/12* (2006.01)

(52) U.S. Cl.
CPC .............. *A61F 13/124* (2013.01); *A61F 9/04* (2013.01); *A61F 13/0226* (2013.01); *A61F 13/0246* (2013.01); *A61F 13/0276* (2013.01)

(58) Field of Classification Search
CPC .... A61F 9/00; A61F 9/02; A61F 9/022; A61F 9/025; A61F 9/026; A61F 9/04; A61F 9/045; A61F 13/124; A61F 13/0226; A61F 13/0246; A61F 13/0276; A61F 13/12; A61F 13/00059; A61F 2013/00421; A61F 2013/00561; A61F 2013/00557; A61F 2013/00655; A61F 2013/00731; A61F 2013/0077; A61F 2013/00761; A61F 2013/00497; A61F 2013/00502; A61F 2013/00744; A61F 2013/00153; A61F 2007/0004
See application file for complete search history.

(56) References Cited

U.S. PATENT DOCUMENTS

| | | | |
|---|---|---|---|
| 3,068,863 A | 12/1962 | Bowman | |
| 3,092,103 A | 6/1963 | Mower | |
| 3,908,645 A | 9/1975 | Sandvig | |
| 4,599,746 A | 7/1986 | Stoner | |
| 4,944,040 A | 7/1990 | Riedel et al. | |
| 5,191,897 A * | 3/1993 | Meshel | A61B 3/00 128/858 |
| 5,429,592 A | 7/1995 | Jensen | |
| 6,320,094 B1 * | 11/2001 | Arnold | A61F 13/124 128/858 |
| 6,890,551 B2 * | 5/2005 | Lenz | A61F 9/04 424/443 |
| 7,584,754 B1 | 9/2009 | Pellegrini et al. | |

(Continued)

FOREIGN PATENT DOCUMENTS

EP 1886655 A2 * 2/2008 ............... A61F 9/04
EP 2473660 B1 * 11/2015 ............ B32B 5/022

*Primary Examiner* — Alireza Nia
*Assistant Examiner* — Rachel A Berezik
(74) *Attorney, Agent, or Firm* — James R. McDaniel

(57) ABSTRACT

A self-adhering occlusion eye patch, wherein the outer non-woven fabric layer is constructed of a spunbond/melt-blown/spunbond non-woven material, an inner black padding layer, wherein the inner black padding layer is constructed of a blend of a spun bound non-woven material and cotton wadding such that the inner black padding layer is attached to the outer non-woven fabric layer, and an inner white non-woven layer having a first side and a second side, wherein the inner white non-woven is constructed of a spun bound non-woven material such that the first side of the inner white non-woven layer is attached to the second side of the inner black padding layer and the second side of the inner white non-woven layer is to be located against an eye of a user.

20 Claims, 3 Drawing Sheets

(56) References Cited

U.S. PATENT DOCUMENTS

| | | | | |
|---|---|---|---|---|
| 7,703,148 B2 * | 4/2010 | Bowers | ............ | A61F 9/04 |
| | | | | 2/12 |
| 2006/0094997 A1 * | 5/2006 | Kurata | ............ | A61F 13/00029 |
| | | | | 602/41 |
| 2009/0104252 A1 * | 4/2009 | Alam | ............ | A61K 33/38 |
| | | | | 424/446 |
| 2014/0308338 A1 * | 10/2014 | Nierle | ............ | A61F 13/025 |
| | | | | 424/448 |
| 2016/0106593 A1 * | 4/2016 | Chandaria | ......... | A61F 13/00059 |
| | | | | 602/52 |

* cited by examiner

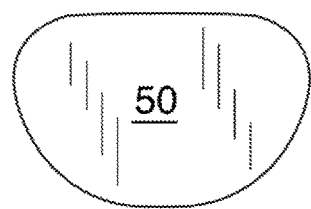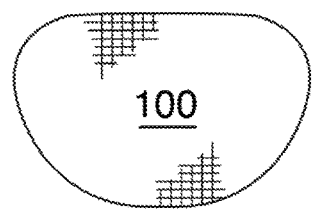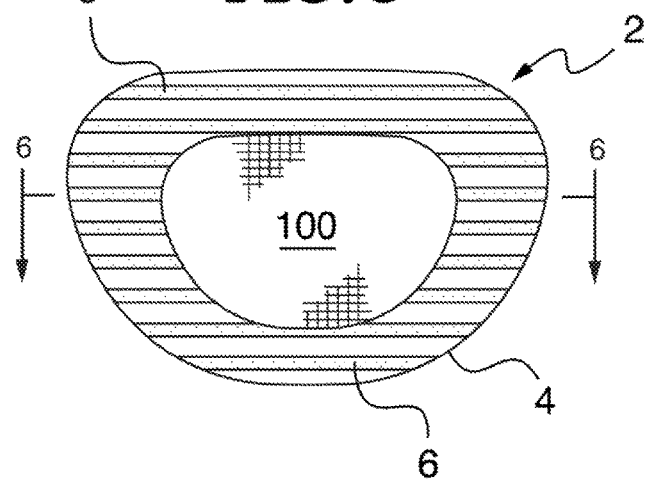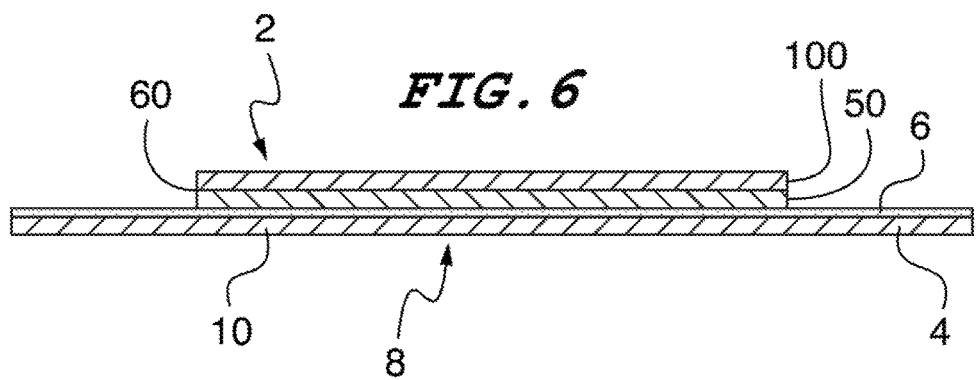

10,258,510 B1

SELF-ADHERING OCCLUSION EYE PATCH AND METHOD OF CONSTRUCTING AND USING SAME

FIELD OF THE INVENTION

The present invention is generally related to a self-adhering occlusion eye patch such that the self-adhering occlusion eye patch has a three-sided diamond shape or rounded triangle shape. In particular, the occlusion eye patch includes a base layer of woven material having a front side screen printed with at least one Food and Drug Administration (FDA) compliant graphical design with a sealant applied over the graphical design, an adhesive layer applied to the entire backside of the base layer such that the adhesive is applied in a horizontal striped arrangement, a black cotton layer is attached on one side to the adhesive layer such that the black layer is smaller in surface area than the base layer, and a white cotton layer is attached to the other side of the black layer such that the black layer and the white layer are approximately 1 mm wide, wherein the white cotton layer is substantially the same in surface area as the black cotton layer. The horizontal striped arrangement of the adhesive creates a self-adhering adhesive surface for the occlusion eye patch that allows the eye patch to be firmly and securely attached to the eye socket area around the eye but also allows the occlusion eye patch to be easily removed. Furthermore, the black layer provides excellent light occlusion properties for the occlusion eye patch. Finally, the overall shape of the self-adhering occlusion eye patch allows the self-adhering occlusion eye patch to be easily and firmly attached to the end user/patient and is comfortable but not too bulky for the end user/patient to wear.

BACKGROUND OF THE INVENTION

A common known eye ailment among both children and adults is called Amblyopia, which is also known as lazy eye. Amblyopia is the most prevalent neurological defect of vision in children and adults, affecting 2-5 percent of the population. Amblyopia is characterized by reduced vision that cannot be corrected by eye glasses or contact lenses and is not the result of an eye disease. Furthermore, amblyopia can cause a loss of depth perception. Early detection (comprehensive eye examinations) and treatment are the best chances for curing amblyopia. Some of the most well-known treatments include eye glasses, eye drops, eye patches and/or vision therapy.

Prior to the present invention, as set forth in general terms above and more specifically below, it is known, to employ various types of eye patches for use in a variety of medical treatments. See for example, U.S. Pat. No. 3,068,863 by Bowman, U.S. Pat. No. 3,092,103 by Mower, U.S. Pat. No. 3,908,645 by Sandvig, U.S. Pat. No. 4,599,746 by Stoner, U.S. Pat. No. 4,944,040 by Riedel et al., U.S. Pat. No. 5,429,592 by Jenson, U.S. Pat. No. 6,890,551 by Lenz et al., and U.S. Pat. No. 7,584,754 by Pellegrini et al. While these various eye patches may have been generally satisfactory, there is nevertheless a need for a new and improved, self-adhering occlusion eye patch which includes a base layer of woven material having a front side screen printed with at least one FDA compliant graphical design with a sealant applied over the graphical design, an adhesive layer applied to the backside of the base layer such that the adhesive is applied in a horizontal striped arrangement, a black cotton layer attached on one side to the adhesive layer such that the black layer is smaller in surface area than the base layer, and a white cotton layer attached to the other side of the black layer such that the black layer and the white layer are approximately 1 mm wide, wherein the white cotton layer is substantially the same in surface area as the black cotton layer.

It is a purpose of this invention to fulfill these and other needs in the eye patch art in a manner more apparent to the skilled artisan once given the following disclosure.

BRIEF SUMMARY OF THE INVENTION

A first aspect of the present invention is a self-adhering occlusion eye patch, including an outer non-woven fabric layer having a first side and a second side, wherein the outer non-woven fabric layer is constructed of a spunbond/meltblown/spunbond non-woven material, an inner black padding layer having a first side and a second side, wherein the inner black padding layer is constructed of a blend of a spun bound non-woven material and cotton wadding such that the first side of the inner black padding layer is attached to the second side of the outer non-woven fabric layer, and an inner white non-woven layer having a first side and a second side, wherein the inner white non-woven is constructed of a spun bound non-woven material such that the first side of the inner white non-woven layer is attached to the second side of the inner black padding layer and the second side of the inner white non-woven layer is to be located against an eye of a user.

In one embodiment of the first aspect of the present invention, the outer non-woven fabric layer further includes at least one graphical design located on the first side of the outer non-woven fabric layer and a sealant layer located over the at least one graphical design such that the sealant layer covers and protects the least one graphical design.

In another embodiment of the first aspect of the present invention, the outer non-woven fabric layer further includes a plurality of adhesive strips located in a horizontal direction on the second side of the outer non-woven fabric layer.

In another embodiment of the first aspect of the present invention, the plurality of adhesive strips is located in a horizontal direction on the second side of the outer non-woven fabric layer such that the adhesive strips are applied in approximately 1-2 mm wide lines with 2-3 mm gaps between the lines.

In another embodiment of the first aspect of the present invention, the outer non-woven fabric layer further includes a 50% spunbond/meltblown/50% spunbond non-woven material.

In still another embodiment of the first aspect of the present invention, the inner black padding layer is constructed of about 30-50% cotton and the inner black padding layer has a light absorbency in the range of between 95-99%.

In an even further embodiment of the first aspect of the present invention, a thickness of the inner black padding layer is between 1-3 mm.

In yet another embodiment of the first aspect of the present invention, a thickness of the inner white non-woven layer is between is between 0.2-0.6 mm.

A second aspect of the present invention is an occlusion eye patch, including an outer non-woven fabric layer having a first side and a second side, wherein the outer non-woven fabric layer is constructed of a spunbond/meltblown/spunbond non-woven material, wherein the outer non-woven fabric layer includes at least one graphical design located on the first side of the outer non-woven fabric layer and a sealant layer located over the at least one graphical design such that the sealant layer covers and protects the least one graphical design, an inner black padding layer having a first side and a second side, wherein the inner black padding layer is constructed of a blend of a spun bound non-woven material and cotton wadding such that the first side of the inner black padding layer is attached to the second side of the outer non-woven fabric layer, and an inner white non-woven layer having a first side and a second side, wherein the inner white non-woven is constructed of a spun bound non-woven material such that the first side of the inner white non-woven layer is attached to the second side of the inner black padding layer and the second side of the inner white non-woven layer is to be located against an eye of a user.

In another embodiment of the second aspect of the present invention, the outer non-woven fabric layer further includes a plurality of adhesive strips located in a horizontal direction on the second side of the outer non-woven fabric layer.

In another embodiment of the second aspect of the present invention, the plurality of adhesive strips is located in a horizontal direction on the second side of the outer non-woven fabric layer such that the adhesive strips are applied in approximately 1-2 mm wide lines with 2-3 mm gaps between the lines.

In another embodiment of the second aspect of the present invention, the outer non-woven fabric layer further includes a 50% spunbond/meltblown/50% spunbond non-woven material.

In still another embodiment of the second aspect of the present invention, the inner black padding layer is constructed of about 30-50% cotton and the inner black padding layer has a light absorbency in the range of between 95-99%.

In an even further embodiment of the second aspect of the present invention, a thickness of the inner black padding layer is between 1-3 mm.

In yet another embodiment of the second aspect of the present invention, a thickness of the inner white non-woven layer is between is between 0.2-0.6 mm.

A third aspect of the present invention is method of constructing a self-adhering occlusion eye patch, including the steps of: providing an outer non-woven fabric layer having a first side and a second side, wherein the outer non-woven fabric layer is constructed of a spunbond/meltblown/spunbond non-woven material; providing an inner black padding layer having a first side and a second side, wherein the inner black padding layer is constructed of a blend of a spun bound non-woven material and cotton wadding such that the first side of the inner black padding layer is attached to the second side of the outer non-woven fabric layer; and providing an inner white non-woven layer having a first side and a second side, wherein the inner white non-woven is constructed of a spun bound non-woven material such that the first side of the inner white non-woven layer is attached to the second side of the inner black padding layer and the second side of the inner white non-woven layer is to be located against an eye of a user.

In one embodiment of the third aspect of the present invention, the step of providing an outer non-woven fabric layer further includes the step of providing at least one graphical design located on the first side of the outer non-woven fabric layer and providing a sealant layer located over the at least one graphical design such that the sealant layer covers and protects the least one graphical design.

In another embodiment of the third aspect of the present invention, the step of providing an outer non-woven fabric layer further includes the step of providing a plurality of adhesive strips located in a horizontal direction on the second side of the outer non-woven fabric layer.

In another embodiment of the third aspect of the present invention, the step of providing a plurality of adhesive strips further includes the step of applying the plurality of adhesive strips in a horizontal direction on the second side of the outer non-woven fabric layer such that the adhesive strips are applied in approximately 1-2 mm wide lines with 2-3 mm gaps between the lines.

In another embodiment of the third aspect of the present invention, the method further includes the step of using an adhesive to attach the first side of the inner white non-woven layer to the second side of the inner black padding layer.

The preferred self-adhering occlusion eye patch, according to various embodiments of the present invention, offers the following advantages: ease of use; lightness in weight; durability; improved comfort; improved graphical designs; improved heat dissipation from the eye through the eye patch; reduction in adhesive marks around the eye socket; improved ability to fit around the eye socket; improved breathability; excellent light occlusion characteristics; excellent self-adhering adhesive characteristics; the three-sided diamond shape or rounded triangle shape of the self-adhering occlusion eye patch; and the ability to use the eye patch on children and adults. In fact, in many of the preferred embodiments, these advantages are optimized to an extent that is considerably higher than heretofore achieved in prior, known eye patches.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 3 is a front view of a black layer of the self-adhering occlusion eye patch, constructed according to the present invention;

FIG. 4 is a front view of a white layer of the self-adhering occlusion eye patch, constructed according to the present invention;

FIG. 5 is rear view of a self-adhering occlusion eye patch after the black and white layers have been attached to the base layer, constructed according to the present invention;

FIG. 6 is side view of the self-adhering occlusion eye patch after the black and white layers have been attached to the base layer, taken along lines 6-6 of FIG. 5, constructed according to the present invention.

DETAILED DESCRIPTION OF THE PREFERRED EMBODIMENTS OF THE INVENTION

In order to address the shortcomings of the prior, known eye patches, reference is made now to FIGS. 1-6, where there is illustrated a self-adhering occlusion eye patch 2 such that the self-adhering occlusion eye patch 2 has a three-sided diamond shape or rounded triangle shape. As will be explained hereinafter in greater detail, the self-adhering occlusion eye patch 2 includes a base layer of woven material having a front side screen printed with at least one FDA compliant graphical design with a sealant applied over the graphical design(s), an adhesive layer applied to the backside of the base layer such that the adhesive is applied in a horizontal striped arrangement, a black cotton layer attached on one side to the adhesive layer such that the black layer is smaller in surface area than the base layer, and a white cotton layer is attached to the other side of the black layer such that the black layer and the white layer combined are approximately 1 mm thick, wherein the white cotton layer is substantially the same in surface area as the black cotton layer. The horizontal striped arrangement of the adhesive creates a self-adherent adhesive surface for the occlusion eye patch that allows the eye patch to be firmly and securely attached to the eye socket area around the eye but also allows the occlusion eye patch to be easily removed. Furthermore, the black layer provides excellent light occlusion properties for the occlusion eye patch.

As shown in FIGS. 1-6, self-adhering occlusion eye patch 2 includes, in part, outer non-woven fabric layer 4, inner black padding layer 50, and inner white non-woven layer 100 (FIG. 6). With respect to outer non-woven fabric layer 4, outer non-woven fabric layer 4 is preferably constructed of a non-woven fabric such as a Spunbond+Meltblown+Spunbond non-woven material. In particular, the preferred non-woven fabric is a 50% Spunbond+Meltblown+50% Spunbond non-woven material. It is to be further understood that the non-woven fabric should be breathable and allow the light to go through to the back side of outer non-woven fabric layer 4.

Figure 1:
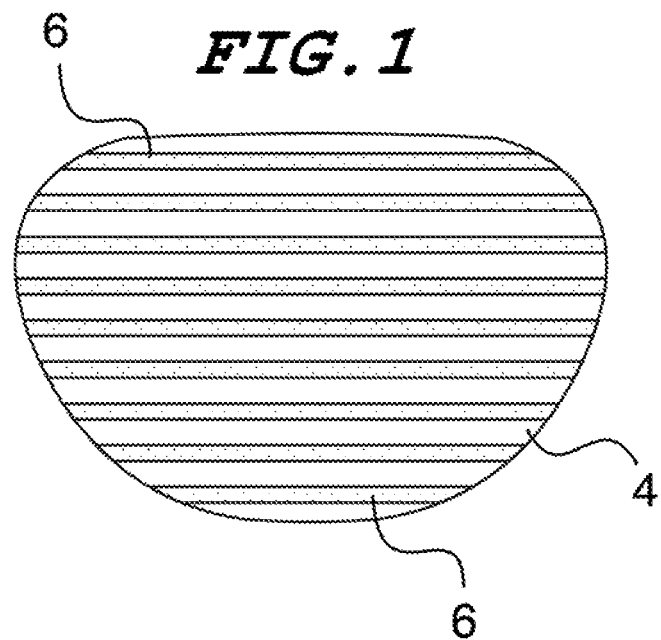
FIG. 1 is a back-side view of a base layer of woven material of the self-adhering occlusion eye patch, constructed according to the present invention.

With respect to outer non-woven fabric layer 4, as shown in FIG. 1, outer non-woven fabric layer 4 includes a plurality of adhesive strips 6 located on the back side of outer non-woven fabric layer 4. Preferably, the adhesive used in the adhesive strips is a gentle adhesive that allows the self-adhering occlusion eye patch 2 to be firmly and securely attached to the area around the eye socket of the patient while also allowing the self-adhering occlusion eye patch 2 to be easily removed from around the eye socket of the patient.

A unique aspect of the present invention is the use of the self-adherent adhesive strips 6 on the outer non-woven fabric layer 4 (FIG. 1). In particular, the adhesive is applied by adhesive application techniques such that adhesive strips 6 are formed in a horizontal direction along the length of the backside of outer non-woven fabric layer 4. Furthermore, the adhesive strips 6 are applied in approximately 1-2 mm width lines with 2-3 mm gaps between the lines. Preferably, the width of adhesive strips 6 is 1 mm and the gap between the adhesive lines is 2 mm. This spacing of the adhesive strips 6 allows the self-adhering occlusion eye patch 2 to be firmly and securely attached to the area around the eye socket of the patient while also allowing the self-adhering occlusion eye patch 2 to be easily removed from around the eye socket of the patient. Also, the use of the gentle adhesive in adhesive strips 6 should not cause any adhesive to be stuck to the eye socket area of the patient once the self-adhering occlusion eye patch 2 is removed. Finally, since the adhesive strips 6 are spaced apart, the entirety of the backside of outer non-woven fabric layer 4 is not attached to the eye socket area of the patient. Consequently, the self-adhering occlusion eye patch 2 can be easily removed without causing any discomfort to the end user.

Figure 2:
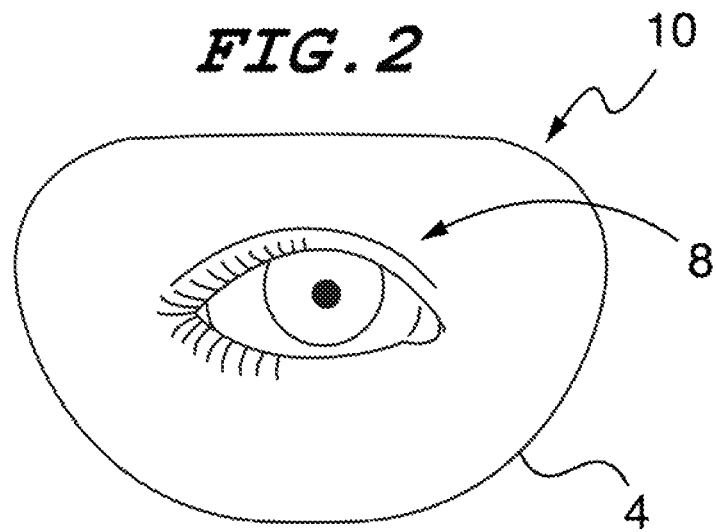
FIG. 2 is a front side view of the base layer of woven material of the self-adhering occlusion eye patch, constructed according to the present invention.

With respect to the front side of outer non-woven fabric layer 4, as shown in FIG. 2, the front side of non-woven fabric layer 4 includes at least one graphical design 8 which is conventionally printed (such as by screen printing) on the front side of non-woven fabric layer 4 with an FDA approved process.

Another unique aspect of the present invention is that the use of at least one graphical design 8 allows a wide variety of self-adhering occlusion eye patches 2 to be produced that will appeal to both children and adults. In particular, graphical designs 8 that appeal to adults can be placed on the front of the self-adhering occlusion eye patches 2 as well as graphical designs 8 that appeal to children can alternatively be placed on the front of the self-adhering occlusion eye patches 2.

Located over the at least one graphical design 8 is a conventional sealant layer 10 (FIGS. 2 and 6). Preferably, sealant layer 10 is constructed of any suitable sealant that covers and protects the at least one graphical design 8 but still allows the non-woven fabric layer 4 to be breathable (i.e., dissipate heat from around the eye socket). It is to be understood that the sealant layer 10 is applied over the at least one graphical design 8 by conventional sealant application techniques such as coating, spraying, rolling, or the like.

A further unique aspect of the present invention is the use of the sealant layer 10. The sealant layer 10 not only protects the at least one graphical design 8 and allows the non-woven fabric layer 4 to be breathable but the sealant layer 10 protects the self-adhering occlusion eye patch 2 against dirt, dust and other debris that comes into contact with the self-adhering occlusion eye patch 2.

Regarding FIG. 3, there is illustrated inner black padding layer 50. Preferably, inner black padding layer 50 is smaller in surface area than non-woven fabric layer 4 and is constructed of a blend of a spun bound non-woven material and cotton wadding that substantially stops any light from entering into the eye upon which the self-adhering occlusion eye patch 2 is located. In particular, the inner black padding layer 50 is constructed of about 30-50% cotton (preferably about 40% cotton). The thickness of inner black padding layer 50 is between 1-3 mm (preferably around 2 mm). Furthermore, the light absorbency (the ability to block light of a preselected wavelength impinging on the self-adhering occlusion eye patch 2) of the inner black padding layer 50 should be between 95-99% (preferably around 98%). In other words, the inner black padding layer 50 is constructed so as to be able to block between 95-99% (preferably around 98%) of any light that impinges upon the self-adhering occlusion eye patch 2. It is to be understood that the inner black padding layer 50 is treated with a FDA approved dye by conventional techniques such as dyeing, dipping, or the like to create the black coloring.

A still further unique aspect of the present invention is the use of the inner black padding layer 50. Inner black padding layer 50 substantially prevents (blocks) any light of a preselected wavelength from entering into the eye upon which the self-adhering occlusion eye patch 2 is located but is thin enough such that the overall size of the self-adhering occlusion eye patch 2 is still relatively thin so that the end user should not experience any discomfort when wearing the self-adhering occlusion eye patch 2 and the self-adhering occlusion eye patch 2 will not look to be too bulky.

With respect to FIG. 4, there is illustrated inner white non-woven layer 100. Preferably, inner white non-woven layer 100 is smaller in surface area than non-woven fabric layer 4. Also, inner white non-woven layer 100 is constructed of a spun bound non-woven material that is breathable and is capable of being located against the eye socket area of the end user. In particular, the inner white non-woven layer 100 is constructed of about 50-70% cotton (preferably about 60% cotton). The thickness of inner white non-woven layer 100 is between 0.2-0.6 mm (preferably around 0.3-0.5 mm). It is to be understood that the surface area of inner white non-woven layer 100 should be approximately the same as the surface area of inner black padding layer 50.

An even further unique aspect of the present invention is the use of the inner white non-woven layer 100. Inner white non-woven layer 100 is breathable but is thin enough such that the overall size of the self-adhering occlusion eye patch 2 is still relatively thin so that the end user should not experience any discomfort when wearing the self-adhering occlusion eye patch 2 and the self-adhering occlusion eye patch 2 will not look to be too bulky. Furthermore, the breathability of inner white non-woven layer 100 allows the self-adhering occlusion eye patch 2 to efficiently dissipate any heat that is created around the eye upon which the self-adhering occlusion eye patch 2 is located.

Regarding the construction of self-adhering occlusion eye patch 2, reference is made to FIGS. 1-6, where there is illustrated self-adhering occlusion eye patch 2 such that the self-adhering occlusion eye patch 2 has a three-sided diamond shape or rounded triangle shape. In order to construct self-adhering occlusion eye patch 2, as discussed earlier, at least one graphical design 8 is attached to the front side of outer non-woven fabric layer 4. A sealant layer 10 is then applied to the front side of outer non-woven fabric layer 4 so that the sealant will cover and protect the at least one graphical design 8. The adhesive strips 6 are then applied to the back side of outer non-woven fabric layer 4.

Once the at least one graphical design 8 and the sealant layer 10 are applied to the front side of outer non-woven fabric layer 4 and the adhesive strips 6 are applied to the back side of outer non-woven fabric layer 4, the inner black padding layer 50 is then centered on the back side of outer non-woven fabric layer 4 and attached to the back side of outer non-woven fabric layer 4 by pressing or forcing one side of inner black padding layer 50 onto the back side of outer non-woven fabric layer 4. It is to be understood that inner black padding layer 50 is retained on the back side of outer non-woven fabric layer 4 by a portion of adhesive strips 6.

After the inner black padding layer 50 has been adhered to the back side of outer non-woven fabric layer 4, the inner white non-woven layer 100 is then conventionally attached to the inner black padding layer 50 by conventional adhesives (adhesive layer 60 in FIG. 6).

A still further unique aspect of the present invention is that the centering of the inner black padding layer 50 and the inner white non-woven layer 100 on the back side of outer non-woven fabric layer 4 (FIG. 5) still allows a portion of adhesive strips 6 to be used to firmly and securely attach self-adhering occlusion eye patch 2 to the eye socket area of the end user but also allows the end user to easily remove the self-adhering occlusion eye patch 2 from the eye socket area of the end user without leaving behind unsightly adhesive remnants around the eye socket area of the end user.

Figure 7:
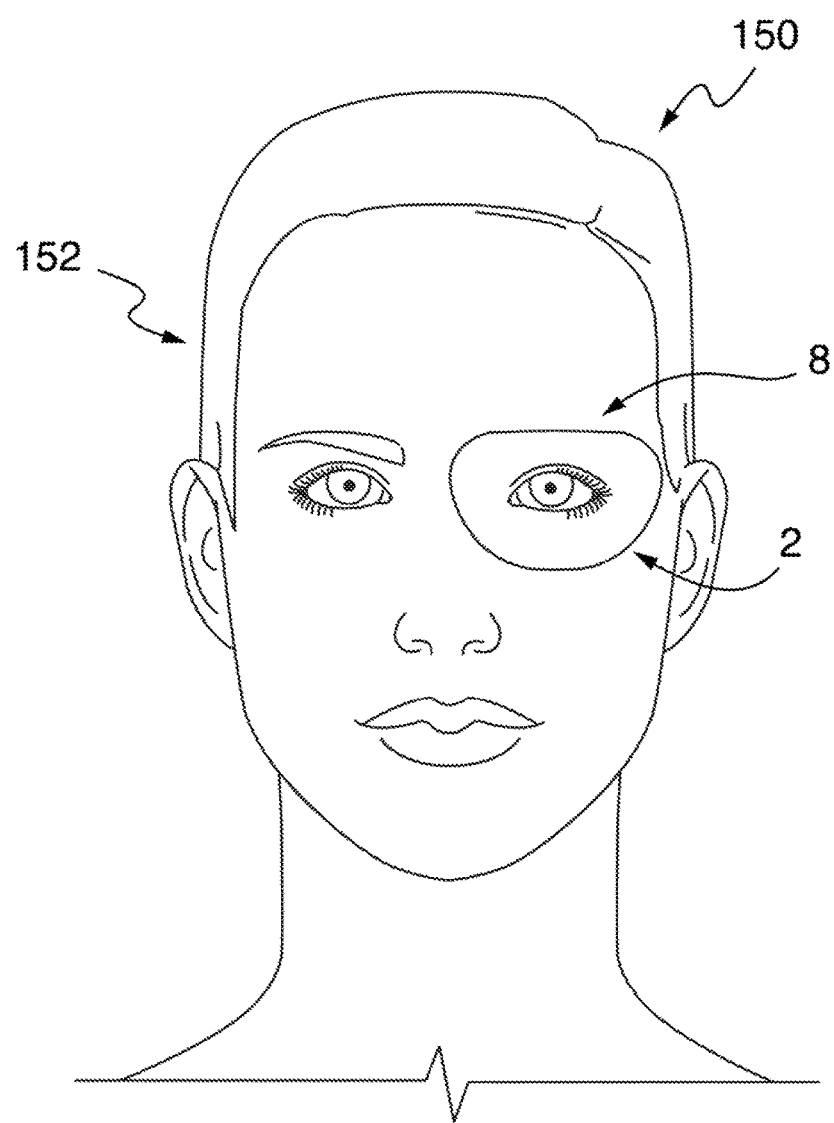
FIG. 7 is a schematic illustration of the self-adhering occlusion eye patch being applied to the eye socket area of a patient, according to the present invention.

With respect to FIG. 7, there is illustrated the occlusion eye patch 2 having a three-sided diamond shape or rounded triangle shape being applied to the eye socket area 152 of a patient/end user 150. As can be seen in FIG. 7, the self-adhering occlusion eye patch 2 can include at least one graphical design 8 that can be tailored to a particular end user such as an adult and/or a child.

Another unique aspect of the present invention is that the self-adhering occlusion eye patch 2 completely fits the area around the eye due to the three-sided diamond shape or rounded triangle shape of the self-adhering occlusion eye patch, but is not of such a size and shape that it creates an unsightly appearance for the end user. It is to be further understood that the overall size of the self-adhering occlusion eye patch 2 can be adjusted so that the self-adhering occlusion eye patch 2 will properly fit either an adult or a child. For example, the overall size of self-adhering occlusion eye patch 2 can be made smaller so that the self-adhering occlusion eye patch 2 can properly fit a child.

A still another unique aspect of the present invention is the overall shape of the self-adhering occlusion eye patch 2. In particular, the overall shape of the self-adhering occlusion eye patch 2 allows the self-adhering occlusion eye patch 2 to be easily and firmly attached to the end user/patient and is comfortable but not too bulky for the end user/patient to wear. This is because the overall shape of the self-adhering occlusion eye patch 2 allows the self-adhering occlusion eye patch 2 to fit more efficiently within the eye socket of the end user/patient due to the very small thickness of the self-adhering occlusion eye patch 2 (the overall thickness of the self-adhering occlusion eye patch 2 is less than 4 mm (preferably less than 3 mm)). Furthermore, the overall shapes of the outer non-woven fabric layer 4, the inner black padding layer 50, and the inner white non-woven layer 100 allow the self-adhering occlusion eye patch 2 to fit more efficiently within the eye socket of the end user/patient. In particular, the outer non-woven fabric layer 4, the inner black padding layer 50, and the inner white non-woven layer 100 are shaped to include a wider portion at the top of the outer non-woven fabric layer 4, the inner black padding layer 50, and the inner white non-woven layer 100 and a narrow potion at the bottom of the outer non-woven fabric layer 4, the inner black padding layer 50, and the inner white non-woven layer 100. Finally, the outer non-woven fabric layer 4, the inner black padding layer 50, and the inner white non-woven layer 100 include curved edges that allow the self-adhering occlusion eye patch 2 to fit more efficiently within the eye socket of the end user/patient.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved self-adhering occlusion eye patch. The preferred self-adhering occlusion eye patch, according to various embodiments of the present invention, offers the following advantages: ease of use; lightness in weight; durability; improved comfort; improved graphical designs; improved heat dissipation from the eye through the eye patch; reduction in adhesive marks around the eye socket; improved ability to fit around the eye socket; improved breathability; excellent light occlusion characteristics; excellent self-adhering adhesive characteristics; the three-sided diamond shape or rounded triangle shape of the self-adhering occlusion eye patch; and the ability to use the eye patch on children and adults. In fact, in many of the preferred embodiments, these advantages of ease of use, lightness in weight, durability, improved comfort, improved graphical designs, improved heat dissipation from the eye through the eye patch, reduction in adhesive marks around the eye socket, improved ability to fit around the eye socket, improved breathability, excellent light occlusion characteristics, excellent self-adhering adhesive characteristics, the three-sided diamond shape or rounded triangle shape of the self-adhering occlusion eye patch, and the ability to use the eye patch on children and adults are optimized to an extent that is considerably higher than heretofore achieved in prior, known eye patches.

I claim:

1. A self-adhering occlusion eye patch, comprising:
   an outer non-woven fabric layer having a first side and a second side, wherein the outer non-woven fabric layer is constructed of a spunbond/meltblown/spunbond non-woven material;
   an inner black padding layer having a first side and a second side, wherein the inner black padding layer is constructed of a blend of a spun bound non-woven material and cotton wadding such that the first side of the inner black padding layer is attached to the second side of the outer non-woven fabric layer such that the inner black padding layer is smaller in surface area than the outer non-woven fabric layer, wherein the inner black padding layer is treated with a dye in order to be able to block between 95-99% of any light that impinges upon the self-adhering occlusion eye patch; and
   an inner white non-woven layer having a first side and a second side such that the inner white non-woven layer is substantially the same in surface area as the inner black padding layer, wherein the inner white non-woven is constructed of a spun bound non-woven material such that the first side of the inner white non-woven layer is attached to the second side of the inner black padding layer and the second side of the inner white non-woven layer is to be located against an eye of a user.

2. The self-adhering occlusion eye patch, according to claim 1, wherein the outer non-woven fabric layer is further comprised of:
   at least one graphical design located on the first side of the outer non-woven fabric layer; and
   a sealant layer located over the at least one graphical design such that the sealant layer covers and protects the least one graphical design.

3. The self-adhering occlusion eye patch, according to claim 1, wherein the outer non-woven fabric layer is further comprised of:
   a plurality of adhesive strips located in a horizontal direction on the second side of the outer non-woven fabric layer.

4. The self-adhering occlusion eye patch, according to claim 3, wherein the plurality of adhesive strips is located in a horizontal direction on the second side of the outer non-woven fabric layer such that the adhesive strips are applied in approximately 1-2 mm wide lines with 2-3 mm gaps between the lines.

5. The self-adhering occlusion eye patch, according to claim 1, wherein the outer non-woven fabric layer is further comprised of:
   a 50% spunbond/meltblown/50% spunbond non-woven material.

6. The self-adhering occlusion eye patch, according to claim 1, wherein the inner black padding layer is constructed of about 30-50% cotton.

7. The self-adhering occlusion eye patch, according to claim 1, wherein a thickness of the inner black padding layer is between 1-3 mm.

8. The self-adhering occlusion eye patch, according to claim 1, wherein a thickness of the inner white non-woven layer is between is between 0.2-0.6 mm.

9. An occlusion eye patch, comprising:
   an outer non-woven fabric layer having a first side and a second side, wherein the outer non-woven fabric layer is constructed of a spunbond/meltblown/spunbond non-woven material, wherein the outer non-woven fabric layer includes at least one graphical design located on the first side of the outer non-woven fabric layer and a sealant layer located over the at least one graphical design such that the sealant layer covers and protects the least one graphical design;
   an inner black padding layer having a first side and a second side, wherein the inner black padding layer is constructed of a blend of a spun bound non-woven material and cotton wadding such that the first side of the inner black padding layer is attached to the second side of the outer non-woven fabric layer such that the inner black padding layer is smaller in surface area than the outer non-woven fabric layer, wherein the inner black padding layer is treated with a dye in order to be able to block between 95-99% of any light that impinges upon the self-adhering occlusion eye patch; and
   an inner white non-woven layer having a first side and a second side such that the inner white non-woven layer is substantially the same in surface area as the inner black padding layer, wherein the inner white non-woven is constructed of a spun bound non-woven material such that the first side of the inner white non-woven layer is attached to the second side of the inner black padding layer and the second side of the inner white non-woven layer is to be located against an eye of a user.

10. The occlusion eye patch, according to claim 9, wherein the outer non-woven fabric layer is further comprised of:
    a plurality of adhesive strips located in a horizontal direction on the second side of the outer non-woven fabric layer.

11. The occlusion eye patch, according to claim 10, wherein the plurality of adhesive strips is located in a horizontal direction on the second side of the outer non-woven fabric layer such that the adhesive strips are applied in approximately 1-2 mm wide lines with 2-3 mm gaps between the lines.

12. The occlusion eye patch, according to claim 9, wherein the outer non-woven fabric layer is further comprised of:
  a 50% spunbond/meltblown/50% spunbond non-woven material.

13. The occlusion eye patch, according to claim 9, wherein the inner black padding layer is constructed of about 30-50% cotton.

14. The occlusion eye patch, according to claim 9, wherein a thickness of the inner black padding layer is between 1-3 mm.

15. The occlusion eye patch, according to claim 9, wherein a thickness of the inner white non-woven layer is between is between 0.2-0.6 mm.

16. A method of constructing a self-adhering occlusion eye patch, comprising the steps of:
  providing an outer non-woven fabric layer having a first side and a second side, wherein the outer non-woven fabric layer is constructed of a spunbond/meltblown/spunbond non-woven material;
  providing an inner black padding layer having a first side and a second side, wherein the inner black padding layer is constructed of a blend of a spun bound non-woven material and cotton wadding such that the first side of the inner black padding layer is attached to the second side of the outer non-woven fabric layer such that the inner black padding layer is smaller in surface area than the outer non-woven fabric layer, wherein the inner black padding layer is treated with a dye in order to be able to block between 95-99% of any light that impinges upon the self-adhering occlusion eye patch; and
  providing an inner white non-woven layer having a first side and a second side such that the inner white non-woven layer is substantially the same in surface area as the inner black padding layer, wherein the inner white non-woven is constructed of a spun bound non-woven material such that the first side of the inner white non-woven layer is attached to the second side of the inner black padding layer and the second side of the inner white non-woven layer is to be located against an eye of a user.

17. The method of constructing a self-adhering occlusion eye patch, according to claim 16, wherein the step of providing an outer non-woven fabric layer is further comprised of the steps of:
  providing at least one graphical design located on the first side of the outer non-woven fabric layer; and
  providing a sealant layer located over the at least one graphical design such that the sealant layer covers and protects the least one graphical design.

18. The method of constructing a self-adhering occlusion eye patch, according to claim 16, wherein the step of providing an outer non-woven fabric layer is further comprised of the step of:
  providing a plurality of adhesive strips in a horizontal direction on the second side of the outer non-woven fabric layer.

19. The method of constructing a self-adhering occlusion eye patch, according to claim 18, wherein the step of providing a plurality of adhesive strips is further comprised of the step of:
  applying the plurality of adhesive strips in the horizontal direction on the second side of the outer non-woven fabric layer such that the adhesive strips are applied in approximately 1-2 mm wide lines with 2-3 mm gaps between the lines.

20. The method of constructing a self-adhering occlusion eye patch, according to claim 16, wherein the method is further comprised of the step of:
  using an adhesive to attach the first side of the inner white non-woven layer to the second side of the inner black padding layer.

\* \* \* \* \*